United States Patent
WasDyke et al.

(10) Patent No.: US 10,405,879 B2
(45) Date of Patent: Sep. 10, 2019

(54) ROTATABLE MEDICAL DEVICE

(71) Applicant: Boston Scientific Scimed, Inc., Maple Grove, MN (US)

(72) Inventors: Joel M. WasDyke, Eden Prairie, MN (US); Tate Augustin, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 782 days.

(21) Appl. No.: 14/955,429

(22) Filed: Dec. 1, 2015

(65) Prior Publication Data
US 2016/0157886 A1 Jun. 9, 2016

Related U.S. Application Data

(60) Provisional application No. 62/087,531, filed on Dec. 4, 2014.

(51) Int. Cl.
| A61B 17/3207 | (2006.01) |
| A61B 17/32 | (2006.01) |
| A61B 17/00 | (2006.01) |
| A61B 17/22 | (2006.01) |

(52) U.S. Cl.
CPC ........ *A61B 17/320758* (2013.01); *A61B 2017/00845* (2013.01); *A61B 2017/22038* (2013.01); *A61B 2017/320004* (2013.01); *A61B 2017/320052* (2013.01)

(58) Field of Classification Search
CPC .. A61B 17/320758; A61B 2017/00845; A61B 2017/22038; A61B 2017/320004; A61B 2017/320052
See application file for complete search history.

(56) References Cited

U.S. PATENT DOCUMENTS

| 4,445,509 A | 5/1984 | Auth |
| 4,684,361 A | 8/1987 | Feldman et al. |
| 4,692,136 A | 9/1987 | Feldman et al. |
| 4,718,888 A | 1/1988 | Darnell |
| 4,990,134 A | 2/1991 | Auth |
| 5,041,082 A | 8/1991 | Shiber |
| 5,181,911 A | 1/1993 | Shturman |
| 5,190,046 A | 3/1993 | Shturman |
| 5,221,258 A | 6/1993 | Shturman |
| 5,295,958 A | 3/1994 | Shturman |
| 5,312,427 A | 5/1994 | Shturman |
| 5,314,407 A | 5/1994 | Auth et al. |
| 5,314,438 A | 5/1994 | Shturman |
| 5,331,947 A | 7/1994 | Shturman |
| 5,356,418 A | 10/1994 | Shturman |

(Continued)

FOREIGN PATENT DOCUMENTS

| WO | 2014160302 A1 | 10/2014 |
| WO | 2015013600 A1 | 1/2015 |

*Primary Examiner* — Julie A Szpira
(74) *Attorney, Agent, or Firm* — Seager, Tufte & Wickhem LLP

(57) ABSTRACT

A rotational atherectomy device advanceable over a guidewire. The rotational atherectomy device includes a drive shaft rotatably extending through an outer tubular member to rotate a cutting member positioned at a distal end thereof. The rotational atherectomy device further includes an insert positioned within the cutting member for frictional contact with the guidewire.

17 Claims, 12 Drawing Sheets

(56) References Cited

U.S. PATENT DOCUMENTS

| | | | |
|---|---|---|---|
| 5,358,485 | A | 10/1994 | Vance et al. |
| 5,360,432 | A | 11/1994 | Shturman |
| 5,443,446 | A | 8/1995 | Shturman |
| 5,490,859 | A | 2/1996 | Mische et al. |
| 5,501,694 | A | 3/1996 | Ressemann et al. |
| 5,554,163 | A | 9/1996 | Shturman |
| 5,584,843 | A | 12/1996 | Wulfman et al. |
| 5,667,490 | A | 9/1997 | Keith et al. |
| 5,672,945 | A | 9/1997 | Krause |
| 5,681,336 | A | 10/1997 | Clement et al. |
| 5,766,190 | A | 6/1998 | Wulfman |
| 5,779,721 | A | 7/1998 | Nash |
| 5,779,722 | A | 7/1998 | Shturman et al. |
| 5,792,157 | A | 8/1998 | Mische et al. |
| 5,836,868 | A | 11/1998 | Ressemann et al. |
| 5,893,857 | A | 4/1999 | Shturman et al. |
| 5,897,566 | A | 4/1999 | Shturman et al. |
| 5,897,567 | A | 4/1999 | Ressemann et al. |
| 5,916,227 | A | 6/1999 | Keith et al. |
| 5,928,218 | A | 7/1999 | Gelbfish |
| 5,938,670 | A | 8/1999 | Keith et al. |
| 6,001,112 | A | 12/1999 | Taylor |
| 6,015,420 | A | 1/2000 | Wulfman et al. |
| 6,024,749 | A | 2/2000 | Shturman et al. |
| 6,027,460 | A | 2/2000 | Shturman |
| 6,039,747 | A | 3/2000 | Shturman et al. |
| 6,077,282 | A | 6/2000 | Shturman et al. |
| 6,080,170 | A | 6/2000 | Nash et al. |
| 6,080,171 | A | 6/2000 | Keith et al. |
| 6,090,122 | A | 7/2000 | Sjostrom et al. |
| 6,126,667 | A * | 10/2000 | Barry ............ A61B 17/320758 606/159 |
| 6,129,734 | A | 10/2000 | Shturman et al. |
| 6,132,444 | A | 10/2000 | Shturman et al. |
| 6,146,395 | A | 11/2000 | Kanz et al. |
| 6,156,048 | A | 12/2000 | Wulfman et al. |
| 6,183,487 | B1 | 2/2001 | Barry et al. |
| 6,206,898 | B1 | 3/2001 | Honeycutt et al. |
| 6,217,595 | B1 | 4/2001 | Shturman et al. |
| 6,221,087 | B1 | 4/2001 | Anderson et al. |
| 6,258,109 | B1 | 7/2001 | Barry et al. |
| 6,270,509 | B1 | 8/2001 | Barry et al. |
| 6,295,712 | B1 | 10/2001 | Shturman et al. |
| 6,328,750 | B1 | 12/2001 | Berry et al. |
| 6,454,779 | B1 | 9/2002 | Taylor |
| 6,482,216 | B1 | 11/2002 | Hiblar et al. |
| 6,494,890 | B1 | 12/2002 | Shturman et al. |
| 6,503,261 | B1 | 1/2003 | Bruneau et al. |
| 6,565,588 | B1 | 5/2003 | Clement et al. |
| 6,579,298 | B1 * | 6/2003 | Bruneau ........ A61B 17/320758 606/159 |
| 6,596,005 | B1 | 7/2003 | Kanz et al. |
| 6,638,288 | B1 | 10/2003 | Shturman et al. |
| 6,818,001 | B2 | 11/2004 | Wulfman et al. |
| 6,852,118 | B2 | 2/2005 | Shturman et al. |
| 6,981,941 | B2 | 1/2006 | Whitman et al. |
| 7,174,240 | B2 | 2/2007 | Shturman et al. |
| 7,175,605 | B2 | 2/2007 | Tiedtke et al. |
| 7,179,269 | B2 | 2/2007 | Welch et al. |
| 7,344,546 | B2 | 3/2008 | Wulfman et al. |
| 7,381,198 | B2 | 6/2008 | Noriega et al. |
| 7,479,147 | B2 | 1/2009 | Honeycutt et al. |
| 7,485,127 | B2 | 2/2009 | Nistal |
| 7,507,245 | B2 | 3/2009 | Shturman et al. |
| 7,534,249 | B2 | 5/2009 | Nash et al. |
| D600,792 | S | 9/2009 | Eubanks et al. |
| 7,584,022 | B2 | 9/2009 | Shturman et al. |
| D607,102 | S | 12/2009 | Robinson |
| D610,258 | S | 2/2010 | Robinson |
| 7,666,202 | B2 | 2/2010 | Prudnikov et al. |
| 7,674,272 | B2 | 3/2010 | Torrance et al. |
| 7,713,231 | B2 | 5/2010 | Wulfman et al. |
| 7,713,235 | B2 | 5/2010 | Torrance et al. |
| 7,842,009 | B2 | 11/2010 | Torrance et al. |
| 8,043,314 | B2 | 10/2011 | Noriega et al. |
| 8,109,954 | B2 | 2/2012 | Shturman |
| 8,109,955 | B2 | 2/2012 | Shturman |
| 8,137,369 | B2 | 3/2012 | Shturman |
| 8,142,458 | B2 | 3/2012 | Shturman |
| 8,147,507 | B2 | 4/2012 | Shturman |
| 8,157,825 | B2 | 4/2012 | Shturman |
| 8,162,964 | B2 | 4/2012 | Piippo et al. |
| 8,177,801 | B2 | 5/2012 | Kallok et al. |
| 8,192,451 | B2 | 6/2012 | Cambronne et al. |
| 8,348,965 | B2 | 1/2013 | Prudnikov et al. |
| 8,353,923 | B2 | 1/2013 | Shturman |
| 8,388,636 | B2 | 3/2013 | Shturman |
| 8,388,637 | B2 | 3/2013 | Shturman |
| 8,439,937 | B2 | 5/2013 | Montague et al. |
| 8,454,638 | B2 | 6/2013 | Shturman |
| 8,465,510 | B2 | 6/2013 | Shturman |
| 8,475,478 | B2 | 7/2013 | Robinson |
| 8,496,678 | B2 | 7/2013 | Shturman |
| 8,500,764 | B2 | 8/2013 | Shturman |
| 8,500,765 | B2 | 8/2013 | Shturman |
| 8,551,128 | B2 | 10/2013 | Hanson et al. |
| 8,551,130 | B2 | 10/2013 | Schoenle et al. |
| 8,568,354 | B2 | 10/2013 | Schoenle et al. |
| 8,568,418 | B2 | 10/2013 | Matusaitis et al. |
| 8,597,313 | B2 | 12/2013 | Thatcher et al. |
| 8,628,550 | B2 | 1/2014 | Narveson |
| 8,628,551 | B2 | 1/2014 | Hanson et al. |
| 8,632,557 | B2 | 1/2014 | Thatcher et al. |
| 8,657,821 | B2 | 2/2014 | Palermo |
| 8,702,735 | B2 | 4/2014 | Rivers |
| 8,758,377 | B2 | 6/2014 | Rivers et al. |
| 8,795,303 | B2 | 8/2014 | McBroom et al. |
| 8,795,304 | B2 | 8/2014 | Piippo Svendsen et al. |
| D721,806 | S | 1/2015 | Higgins et al. |
| 8,974,519 | B2 | 3/2015 | Gennrich et al. |
| 2002/0082637 | A1 | 6/2002 | Lumauig |
| 2003/0078594 | A1 | 4/2003 | Shturman et al. |
| 2003/0120296 | A1 | 6/2003 | Shturman et al. |
| 2003/0125756 | A1 | 7/2003 | Shturman et al. |
| 2003/0139689 | A1 | 7/2003 | Shturman et al. |
| 2004/0006358 | A1 | 1/2004 | Wulfman et al. |
| 2004/0181249 | A1 | 9/2004 | Torrance et al. |
| 2004/0220519 | A1 | 11/2004 | Wulfman et al. |
| 2004/0230212 | A1 | 11/2004 | Wulfman |
| 2004/0230213 | A1 | 11/2004 | Wulfman et al. |
| 2004/0235611 | A1 | 11/2004 | Nistal |
| 2004/0236312 | A1 | 11/2004 | Nistal et al. |
| 2004/0243162 | A1 | 12/2004 | Wulfman et al. |
| 2005/0149083 | A1 | 7/2005 | Prudnikov et al. |
| 2006/0235453 | A1 | 10/2006 | Shturman et al. |
| 2006/0249205 | A1 | 11/2006 | Shturman et al. |
| 2006/0258976 | A1 | 11/2006 | Shturman et al. |
| 2006/0271242 | A1 | 11/2006 | Shturman et al. |
| 2007/0225615 | A1 | 9/2007 | Chechelski et al. |
| 2008/0103439 | A1 | 5/2008 | Torrance et al. |
| 2008/0103446 | A1 | 5/2008 | Torrance et al. |
| 2008/0103516 | A1 | 5/2008 | Wulfman et al. |
| 2008/0228208 | A1 | 9/2008 | Wulfman et al. |
| 2008/0306498 | A1 | 12/2008 | Thatcher et al. |
| 2008/0319462 | A1 | 12/2008 | Montague et al. |
| 2009/0012548 | A1 | 1/2009 | Thatcher et al. |
| 2009/0018564 | A1 | 1/2009 | Shturman |
| 2009/0069829 | A1 | 3/2009 | Shturman |
| 2009/0105736 | A1 | 4/2009 | Prudnikov et al. |
| 2009/0149877 | A1 | 6/2009 | Hanson et al. |
| 2009/0182359 | A1 | 7/2009 | Shturman |
| 2009/0264908 | A1 | 10/2009 | Kallok et al. |
| 2009/0299391 | A1 | 12/2009 | Rivers et al. |
| 2009/0299392 | A1 | 12/2009 | Rivers |
| 2009/0306657 | A1 | 12/2009 | Piippo et al. |
| 2009/0306689 | A1 | 12/2009 | Welty et al. |
| 2009/0306690 | A1 | 12/2009 | Rivers et al. |
| 2009/0306691 | A1 | 12/2009 | Cambronne et al. |
| 2009/0312777 | A1 | 12/2009 | Shturman |
| 2009/0318942 | A1 | 12/2009 | Shturman |
| 2009/0326568 | A1 | 12/2009 | Shturman |
| 2010/0010522 | A1 | 1/2010 | Shturman |
| 2010/0036402 | A1 | 2/2010 | Hanson et al. |
| 2010/0049226 | A1 | 2/2010 | Shturman |

(56) References Cited

U.S. PATENT DOCUMENTS

| | | |
|---|---|---|
| 2010/0100110 A1 | 4/2010 | Cambronne et al. |
| 2010/0121361 A1 | 5/2010 | Plowe et al. |
| 2010/0198239 A1 | 8/2010 | McBroom et al. |
| 2010/0211088 A1 | 8/2010 | Narveson |
| 2010/0253552 A1 | 10/2010 | Lanceros Mendez et al. |
| 2010/0292720 A1 | 11/2010 | Thatcher et al. |
| 2010/0324472 A1 | 12/2010 | Wulfman |
| 2011/0009888 A1 | 1/2011 | Shturman |
| 2011/0040238 A1 | 2/2011 | Wulfman et al. |
| 2011/0071440 A1 | 3/2011 | Torrance et al. |
| 2011/0077673 A1 | 3/2011 | Grubac et al. |
| 2011/0087254 A1 | 4/2011 | Welty |
| 2011/0106004 A1 | 5/2011 | Eubanks et al. |
| 2011/0112562 A1 | 5/2011 | Torrance |
| 2011/0118660 A1 * | 5/2011 | Torrance ........ A61B 17/320758 604/35 |
| 2011/0144671 A1 | 6/2011 | Piippo Svendsen et al. |
| 2011/0151463 A1 | 6/2011 | Wulfman |
| 2011/0202079 A1 | 8/2011 | Schoenle et al. |
| 2011/0208221 A1 | 8/2011 | Gennrich et al. |
| 2011/0213391 A1 | 9/2011 | Rivers et al. |
| 2011/0300010 A1 | 12/2011 | Jarnagin et al. |
| 2012/0035588 A1 | 2/2012 | Schoenle et al. |
| 2012/0035633 A1 | 2/2012 | Shturman |
| 2012/0041359 A1 | 2/2012 | Schoenle et al. |
| 2012/0046599 A1 | 2/2012 | Schoenle et al. |
| 2012/0046600 A1 | 2/2012 | Kohler et al. |
| 2012/0109105 A1 | 5/2012 | Cambronne |
| 2012/0109170 A1 | 5/2012 | Shturman |
| 2012/0116431 A1 | 5/2012 | Shturman |
| 2012/0150207 A1 | 6/2012 | Shturman |
| 2012/0165846 A1 | 6/2012 | Shturman |
| 2012/0165847 A1 | 6/2012 | Shturman |
| 2012/0172903 A1 | 7/2012 | Shturman |
| 2012/0179179 A1 | 7/2012 | Shturman |
| 2012/0191113 A1 | 7/2012 | Shturman |
| 2013/0018398 A1 | 1/2013 | Rivers et al. |
| 2013/0018399 A1 | 1/2013 | Rivers et al. |
| 2013/0023913 A1 | 1/2013 | Rivers et al. |
| 2013/0178881 A1 | 7/2013 | Shturman |
| 2013/0204280 A1 | 8/2013 | Shturman |
| 2013/0245654 A1 | 9/2013 | Shturman |
| 2013/0253552 A1 | 9/2013 | Schoenle et al. |
| 2013/0274773 A1 | 10/2013 | Shturman et al. |
| 2013/0296904 A1 | 11/2013 | Shturman et al. |
| 2013/0296905 A1 | 11/2013 | Shturman |
| 2013/0310859 A1 | 11/2013 | Shturman |
| 2014/0081298 A1 | 3/2014 | Cambronne |
| 2014/0277014 A1 | 9/2014 | Higgins et al. |
| 2014/0316447 A1 | 10/2014 | Ellering et al. |
| 2014/0316448 A1 | 10/2014 | Higgins |
| 2014/0316449 A1 | 10/2014 | Grothe et al. |
| 2014/0316450 A1 | 10/2014 | Higgins |
| 2014/0316451 A1 | 10/2014 | Higgins et al. |
| 2014/0350582 A1 | 11/2014 | Higgins |
| 2014/0364883 A1 | 12/2014 | Schoenle et al. |
| 2014/0365691 A1 | 12/2014 | Schoenle et al. |
| 2014/0371770 A1 | 12/2014 | Schoenle et al. |
| 2015/0005791 A1 | 1/2015 | Schoenle et al. |
| 2015/0051626 A1 | 2/2015 | Rivers et al. |
| 2015/0073447 A1 | 3/2015 | Rydberg et al. |
| 2015/0073448 A1 | 3/2015 | Rydberg |
| 2015/0080747 A1 | 3/2015 | Schoenle |
| 2015/0080795 A1 | 3/2015 | Mattison et al. |
| 2015/0089785 A1 | 4/2015 | Blackledge et al. |
| 2015/0094745 A1 | 4/2015 | Blackledge et al. |
| 2015/0094749 A1 | 4/2015 | Ellering et al. |
| 2015/0112371 A1 | 4/2015 | Rydberg et al. |
| 2015/0119909 A1 | 4/2015 | Rydberg |
| 2015/0127033 A1 | 5/2015 | Rydberg et al. |
| 2015/0133974 A1 | 5/2015 | Karasti et al. |
| 2015/0133975 A1 | 5/2015 | Rydberg et al. |
| 2015/0133976 A1 | 5/2015 | Johnson et al. |
| 2015/0142027 A1 | 5/2015 | Rydberg et al. |
| 2015/0142028 A1 | 5/2015 | Ellering et al. |

* cited by examiner

ROTATABLE MEDICAL DEVICE

CROSS-REFERENCE TO RELATED APPLICATIONS

This application claims priority under 35 U.S.C. § 119 to U.S. Provisional Application Ser. No. 62/087,531, filed Dec. 4, 2014, the entirety of which is incorporated herein by reference.

TECHNICAL FIELD

The disclosure is directed to devices and methods for removing occlusive material from a body lumen. More particularly, the disclosure is directed to a rotational atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a rotatable cutting element thereon is advanced through the occlusion to form or enlarge a pathway through the occlusion. Typically, a guidewire is initially placed across the occlusion and then the atherectomy catheter is advanced over the guidewire as the atherectomy catheter is passed through the occlusion.

A need remains for alternative atherectomy devices to facilitate crossing an occlusion while being advanced along a guidewire.

BRIEF SUMMARY

The disclosure is directed to several alternative designs, materials and methods of manufacturing medical device structures and assemblies, and uses thereof.

Accordingly, one illustrative example is a rotational atherectomy device. The rotational atherectomy device includes an outer tubular member having a lumen extending therethrough, a cutting member rotationally positioned at a distal end of the outer tubular member, and a drive shaft extending through the lumen of the outer tubular member. The drive shaft is rotatable relative to the outer tubular member to rotate the cutting member. The rotational atherectomy device further includes an insert positioned within the cutting member, the insert including an opening extending therethrough for passing a guidewire therethrough.

Additionally or alternatively, a distal portion of the drive shaft extends into a bore of the cutting member.

Additionally or alternatively, the insert is positioned in the bore of the cutting member distal of a distal end of the drive shaft.

Additionally or alternatively, the drive shaft includes a guidewire lumen extending therethrough axially aligned with the opening of the insert.

Additionally or alternatively, the guidewire lumen has a diameter and the opening of the insert has a diameter less than the diameter of the guidewire lumen.

Additionally or alternatively, the insert includes an inner surface defining the opening of the insert, wherein at least a portion of the inner surface is nonparallel to a central longitudinal axis of the drive shaft.

Additionally or alternatively, the inner surface tapers radially outward from the central longitudinal axis in a distal direction.

Additionally or alternatively, the inner surface tapers radially outward in a distal direction from a mid region of the insert to a distal tip of the insert.

Additionally or alternatively, the inner surface tapers radially outward in a proximal direction from the mid region of the insert to a proximal end of the insert.

Additionally or alternatively, the bore has a diameter greater than the diameter of the opening of the insert.

Additionally or alternatively, the insert includes an inner surface defining the opening of the insert, the inner surface having a surface roughness $R_a$ of 0.4 micrometers or less.

Additionally or alternatively, the insert includes an inner surface defining the opening of the insert, the inner surface having a surface roughness $R_a$ of 0.2 micrometers or less.

Additionally or alternatively, the cutting member includes a distal opening axially aligned with the opening of the insert, the distal opening of the cutting member having a diameter greater than or equal to a diameter of the opening of the insert.

Additionally or alternatively, the insert is formed of a polymeric material.

Additionally or alternatively, the insert is formed of a polished metallic material.

An illustrative example that may optionally be used in conjunction with any of the above described characteristics is a rotational atherectomy device. The rotational atherectomy device includes an outer tubular member having a lumen extending therethrough, a cutting member rotationally positioned at a distal end of the outer tubular member, and a drive shaft extending through the lumen of the outer tubular member. The cutting member includes a central longitudinal bore extending therethrough. A distal end region of the drive shaft extends into the bore of the cutting member. The drive shaft is rotatable relative to the outer tubular member to rotate the cutting member. The rotational atherectomy device further includes an insert positioned within the bore of the cutting member. The insert includes an opening extending therethrough axially aligned with the bore of the cutting member.

Additionally or alternatively, the drive shaft includes a guidewire lumen extending therethrough axially aligned with the opening of the insert.

Additionally or alternatively, the guidewire lumen has a diameter and the opening of the insert has a diameter less than the diameter of the guidewire lumen.

Additionally or alternatively, the cutting member includes a distal opening axially aligned with the opening of the insert, the distal opening of the cutting member having a diameter greater than or equal to a diameter of the opening of the insert.

Additionally or alternatively, the insert includes an inner surface defining the opening of the insert, wherein at least a portion of the inner surface is nonparallel to a central longitudinal axis of the drive shaft.

Additionally or alternatively, the insert includes an inner surface defining the opening of the insert, the inner surface having a surface roughness $R_a$ of 0.4 micrometers or less.

Another illustrative example is method of creating or enlarging a passageway through an occlusion in a body lumen. The method includes advancing a guidewire through a body lumen to a location proximate an occlusion and then advancing a rotational atherectomy device through the body lumen over the guidewire to a location proximal of the occlusion in the body lumen. The rotational atherectomy device includes a rotatable drive shaft extending through an outer tubular member to rotatably drive a cutting member positioned at a distal end of the outer tubular member, and an insert positioned within the cutting member. The guidewire extends through an opening of the insert and a guidewire lumen of the drive shaft. The method further includes rotating the cutting member relative to the guidewire with the drive shaft while advancing the cutting member through the occlusion.

Additionally or alternatively, a coefficient of static friction between the insert and the guidewire is less than 0.25.

Additionally or alternatively, a coefficient of static friction between the insert and the guidewire is less than 0.10.

BRIEF DESCRIPTION OF THE DRAWINGS

The aspects of the disclosure may be more completely understood in consideration of the following detailed description of various embodiments in connection with the accompanying drawings, in which.

Figure 1:
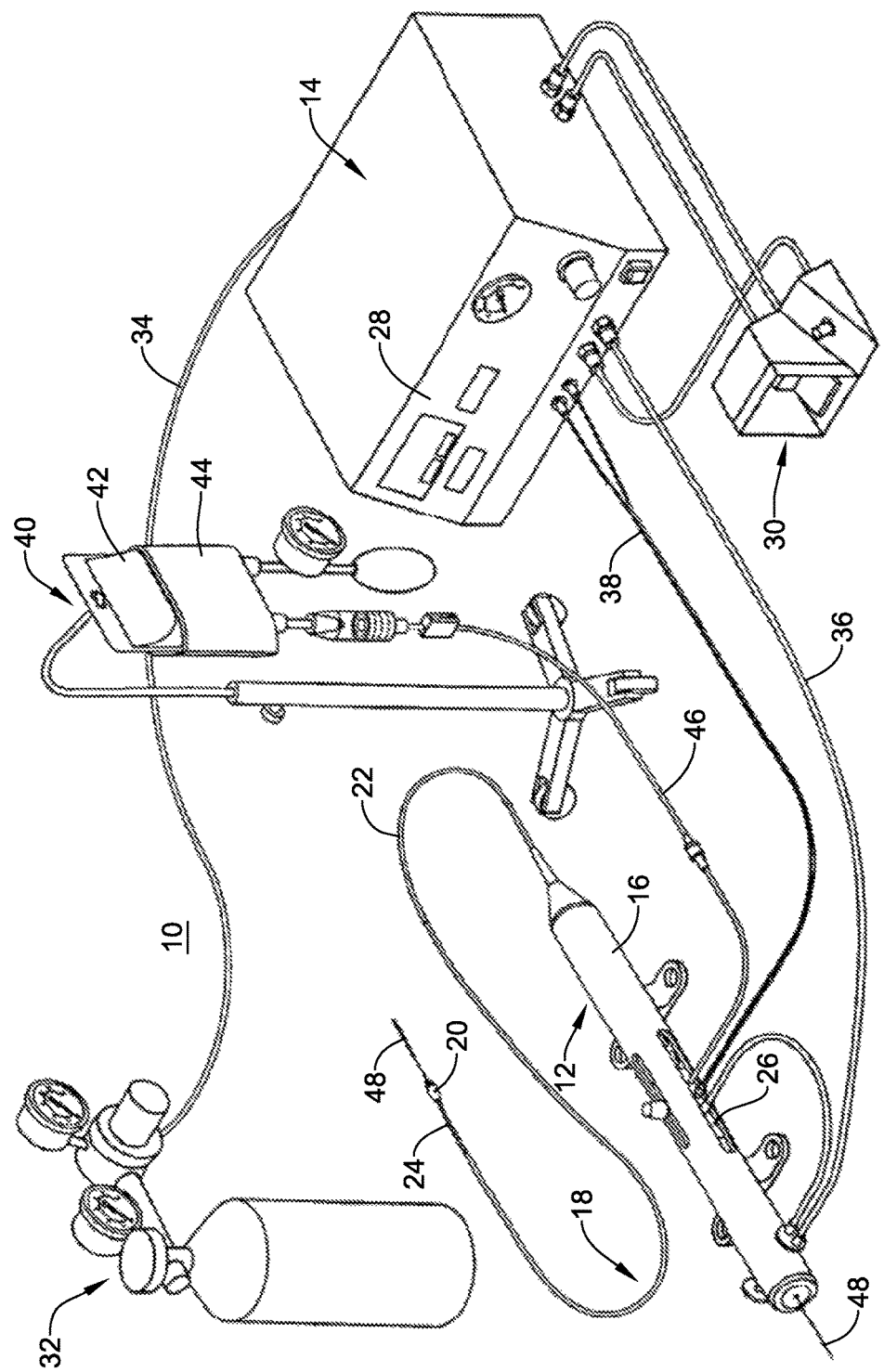
FIG. 1 illustrates an exemplary atherectomy system.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary rotational atherectomy system 10 is shown in FIG. 1. The rotational atherectomy system 10 may include a rotational atherectomy device 12 and a controller 14 for controlling the rotational atherectomy device 12. The rotational atherectomy device 12 may include a housing 16 and an elongate shaft 18 extending distally from the housing 16 to a cutting member 20 located at a distal end of the elongate shaft 18. The elongate shaft 18 may include a drive shaft 24 to provide rotational motion to the cutting member 20. In some instances, the elongate shaft 18 may include an outer tubular member 22 having a lumen extending therethrough and the drive shaft 24 may extend through the lumen of the outer tubular member 22. The drive shaft 24, which may be fixed to the cutting member 20, may be rotatable relative to the outer tubular member 22 to rotate the cutting member 20. In some instances the axial position of the cutting member 20 relative to the outer tubular member 22 may be adjusted by moving the drive shaft 24 longitudinally relative to the outer tubular member 22. For example, the atherectomy device 12 may include an advancer assembly 26 positioned in the housing 16, or otherwise provided with the housing 16, that is longitudinally movable relative to the housing 16. The outer tubular member 22 may be coupled to the housing 16 while the drive shaft 24 may be coupled to the advancer assembly 26. Accordingly, the drive shaft 24 (and thus the cutting member 20) may be longitudinally movable relative to the outer tubular member 22 by actuating the advancer assembly 26 relative to the housing 16.

The rotational atherectomy device 12 may include a prime mover (not shown) to provide rotational motion to the drive shaft 24 to rotate the cutting member 20. For example, in some instances the prime mover may be a fluid turbine within the housing 16, such as provided with the advancer assembly 26. In other instances, however, the prime mover may be an electrical motor, or the like. The controller 14 may be used to control the prime mover. For example, the user may provide power to the prime mover and/or control the speed of rotation of the drive shaft 24 via the controller 14. For example, the front panel 28 of the controller 14 may include a user interface including a power switch, speed control mechanism (e.g., a speed control knob and/or buttons), a display, and/or other features for controlling the rotational atherectomy device 12. In some instances, the rotational atherectomy system 10 may include a remote control device 30, such as a foot pedal, a hand control, or other mechanism which may be used to control the power and/or speed to the prime mover, for example.

In instances in which the prime mover is a turbine, the rotational atherectomy system 10 may also include a pressurized fluid source 32 providing a pressurized fluid to the turbine to rotate the drive shaft 24. In some instances, as shown, the pressurized fluid source 32 may be a tank of pressurized fluid (e.g., compressed air), which may or may not include an air compressor. In other instances, the pressured fluid source 32 may be provided external of the rotational atherectomy system 10, such as from a wall outlet at the medical facility. The pressured fluid source 32 may be coupled to the controller 14 via a fluid conduit 34, which in turn is coupled to the rotational atherectomy device 12 via a fluid conduit 36. The controller 14 may regulate the flow and/or pressure of fluid through the fluid conduit 36 to the rotational atherectomy device 12 to control the speed of rotation of the drive shaft 24 and cutting member 20, for instance.

In instances in which the prime mover is an electric motor, the electric motor may be coupled to the controller 14 via an electrical connection to control the electric motor and/or provide electricity to the electric motor.

In some instances, the rotational atherectomy device 12 may include a speed sensor, such as an optical speed sensor, coupled to the controller 14 via a connector 38, such as a fiber optic connector to provide speed data to the controller 14. In other instances, an electronic sensor, such as a Hall Effect sensor, or other type of sensor may be used to sense the speed of the drive shaft 24 and cutting member 20. The speed data may be displayed, such as on the front panel 28 and/or the controller 14, and/or used to control the speed of the cutting member 20, such as maintaining a desired speed of the cutting member 20 during a medical procedure.

In some embodiments, the rotational atherectomy system 10 may be configured to infuse fluid through the elongate shaft 18 to the treatment site and/or aspirate fluid through the elongate shaft 18 from the treatment site. For example, the rotational atherectomy system 10 may include a fluid supply 40 for providing a flow of fluid through a lumen of the elongate shaft 18 to a treatment site. As shown in FIG. 1, in some instances the fluid supply 40 may include a saline bag 42 which may be pressurized by a pressure cuff 44 to provide a pressurized fluid (e.g., saline) to the rotational atherectomy device 12 through a fluid supply line 46. In other embodiments, an infusion pump, such as a peristaltic pump, may be used to deliver pressurized fluid to the rotational atherectomy device 12. Additionally or alternatively, in some embodiments the rotational atherectomy system 10 may be configured to aspirate fluid from the treatment site. For example, the rotational atherectomy system 10 may include an aspiration pump, such as a peristaltic pump, to generate a vacuum to aspirate fluid through a lumen of the elongate shaft 18 to a fluid collection container (not shown), if desired.

In some instances, the elongate shaft 18 of the rotational atherectomy device 12 may be advanced over a guidewire 48 to a treatment site. For example, the drive shaft 24 may include a guidewire lumen through which the guidewire 48 may pass. Additionally or alternatively, the elongate shaft 18 may be advanced through a lumen of a guide catheter to a treatment site.

Figure 2:
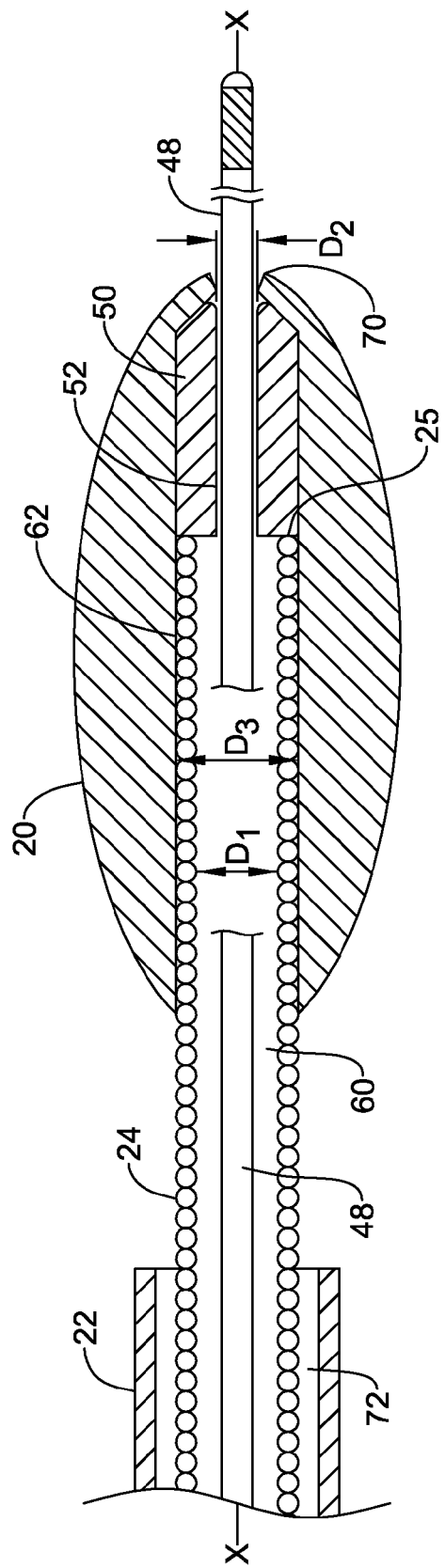
FIG. 2 is a cross-sectional view of a distal portion of an exemplary atherectomy system in accordance with the disclosure.

The distal region of the rotational atherectomy device 12 is shown in FIG. 2. As shown, the drive shaft 24, which in some instances may include a coiled member, may extend through the lumen 72 of the outer tubular member 22 and be rotationally and/or longitudinally movable relative to the outer tubular member 22. The drive shaft 24 may include the cutting member 20 mounted thereon. In some instances, the cutting member 20 may be a burr having an abrasive surface, such as a diamond coated abrasive surface. In other instances, the cutting member 20 may include one or more flutes having a cutting edge, or the cutting member 20 may be of another construction for abrading or cutting occlusive material.

A guidewire lumen 60 may extend through the drive shaft 24 and the cutting member 20 to a distal tip 70 of the cutting member 20. As shown, the cutting member 20 may include a bore 62 extending therethrough with a distal end region of the drive shaft 24 extending into the bore 62 of the cutting member 20.

The rotational atherectomy device 12 may also include an insert 50 positioned within the cutting member 20. For example, the insert 50 may be positioned in the bore 62 of the cutting member 20 distal of a distal end 25 of the drive shaft 24. The insert 50 may include an opening 52 extending therethrough for passing the guidewire 48 therethrough. In some instances, the opening 52 through the insert 50 may be axially aligned with the guidewire lumen 60 of the drive shaft 24. In other words, the opening 52 may be coaxial with the guidewire lumen 60 in some instances.

The guidewire lumen 60 may have a diameter $D_1$ and the opening 52 through the insert 50 may have a diameter $D_2$. In some instances, the diameter $D_1$ of the guidewire lumen 60 may be greater than the diameter $D_2$ of the opening 52. Accordingly, there may be a closer tolerance between an inner surface of the insert 50 and the guidewire 48 than the tolerance between the guidewire 48 and the drive shaft 24. In other words, there may be greater clearance between the guidewire 48 and the inner surface of the drive shaft 24 than the clearance between the guidewire 48 and the inner surface of the insert 50 defining the opening 52. For example, to accommodate a guidewire having an outer diameter of 0.36 millimeter (0.014 inches), the guidewire lumen 60 may have a diameter $D_1$ of about 0.41 millimeters (0.016 inches) or more, or about 0.46 millimeters (0.018 inches) or more, while the diameter $D_2$ of the opening 52 of the insert 50 may be about 0.38 millimeters (0.015 inches).

The bore 62, within which the insert 50 and/or the distal end region of the drive shaft 24 may be disposed, may have a diameter $D_3$. The diameter $D_3$ of the bore 62 may be greater than the diameter $D_1$ of the guidewire lumen 60 through the drive shaft 24 and/or the opening 52 through the insert 50. In some instances, the insert 50 may be inserted into the bore 62 of the cutting member 20 from the proximal opening of the cutting member 20. Thereafter, the distal end region of the drive shaft 24 may be inserted into the bore 62 of the cutting member 20 from the proximal opening of the cutting member 20. In some instances, the distal end 25 of the drive shaft 24 may face or abut the proximal end of the insert 50 within the bore 62 of the cutting member 20.

The cutting member 20 may include a distal opening at the distal tip 70 of the cutting member 20. The distal opening of the cutting member 20 may be axially aligned with the opening 52 of the insert 50. In some instances, the distal opening of the cutting member 20 may have a diameter greater than or equal to the diameter $D_2$ of the opening 52 of the insert 50. In some instances, the distal opening of the cutting member 20 may be configured to facilitate inserting the guidewire 48 into the opening 52 of the insert 50 and through the guidewire lumen 62 of the drive shaft 24 from the distal tip 70 of the cutting member 20.

In some instances, the insert 50 may function as a spacer and/or bearing between the cutting member 20 and the guidewire 48. For example, the insert 50 may provide a low friction interface with the guidewire 48 as the cutting member 20 is rotatably driven during a medical procedure.

In some instances, the inner surface of the insert 50 which defines the opening 52 of the insert 50 may have an average surface roughness $R_a$ of about 0.4 micrometers or less, about 0.3 micrometers or less, about 0.2 micrometers or less, or about 0.1 micrometers or less. Additionally or alternatively, in some instances the coefficient of static friction $\mu_s$ between the insert 50 and the guidewire 48 may be less than 0.25, less than 0.20, less than 0.15 or less than 0.10, for example.

The insert 50 may be made of any desired material, such as a low friction material, including a metallic material, a polymeric material, or a combination thereof. Some suitable metallic materials include stainless steel, such as highly polished stainless steel. Some suitable polymeric materials include polyamide (e.g., nylon), polytetrafluoroethylene (PTFE), high density polyethylene (HDPE), ultra-high molecular weight polyethylene (UHMWPE), or other polymeric material having a high molecular weight, for example.

Figure 3:
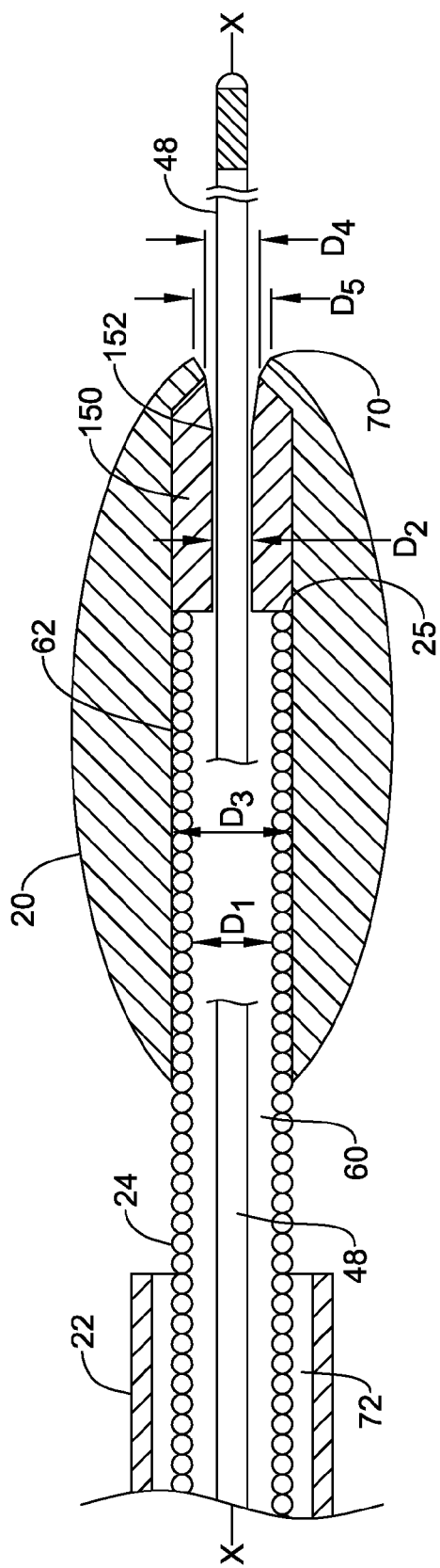
FIG. 3 is a cross-sectional view of a distal portion of another exemplary atherectomy system in accordance with the disclosure.

Another embodiment of the distal region of the rotational atherectomy device 12 is shown in FIG. 3. The components and arrangement of the distal region may be similar in many respects to that shown in FIG. 2, and thus reference to those aspects discussed above is noted. As shown in FIG. 3, an insert 150 may be positioned within the cutting member 20. For example, the insert 150 may be positioned in the bore 62 of the cutting member 20 distal of a distal end 25 of the drive shaft 24. The insert 150 may include an opening 152 extending therethrough for passing the guidewire 48 therethrough. In some instances, the opening 152 through the insert 150 may be axially aligned with the guidewire lumen 60 of the drive shaft 24. In other words, the opening 152 may be coaxial with the guidewire lumen 60 in some instances.

The insert 150 may include an inner surface defining the opening 152 of the insert 150. As shown in FIG. 3, at least a portion of the inner surface of the insert 150 may be nonparallel to the central longitudinal axis X of the drive shaft 24. For example, the inner surface of the insert 150 may taper radially outward from the central longitudinal axis in a distal direction (i.e., flare radially outward toward the distal tip 70) along at least a portion of the longitudinal length of the opening 152. For example, a proximal region and/or mid region of the opening 152 may have a diameter $D_2$, while a distal region of the opening 152 may have a diameter $D_4$ greater than the diameter $D_2$ of the proximal region and/or mid region of the opening 152.

The insert 150 may be similar to the insert 50 described above. For example, the insert 150 may function as a spacer and/or bearing between the cutting member 20 and the guidewire 48. For example, the insert 150 may provide a low friction interface with the guidewire 48 as the cutting member 20 is rotatably driven during a medical procedure.

In some instances, the inner surface of the insert 150 which defines the opening 152 of the insert 150 may have an average surface roughness $R_a$ of about 0.4 micrometers or less, about 0.3 micrometers or less, about 0.2 micrometers or less, or about 0.1 micrometers or less. Additionally or alternatively, in some instances the coefficient of static friction $\mu_s$ between the insert 150 and the guidewire 48 may be less than 0.25, less than 0.20, less than 0.15 or less than 0.10, for example.

The insert 150 may be made of any desired material, such as a low friction material, including a metallic material, a polymeric material, or a combination thereof. Some suitable metallic materials include stainless steel, such as highly polished stainless steel. Some suitable polymeric materials include polyamide (e.g., nylon), polytetrafluoroethylene (PTFE), high density polyethylene (HDPE), ultra-high molecular weight polyethylene (UHMWPE), or other polymeric material having a high molecular weight, for example.

Also shown in FIG. 3, the distal opening of the cutting member 20 at the distal tip 70 may have a diameter $D_5$ greater than the diameter $D_4$ of the distal region of the opening 152, and thus greater than the diameter $D_2$ of the proximal region and/or mid region of the opening 152. The enlarged diameter of the distal opening of the cutting member 20 may facilitate inserting the guidewire 48 into the opening 152 of the insert 150 and through the guidewire lumen 62 of the drive shaft 24 from the distal tip 70 of the cutting member 20.

Figure 4:
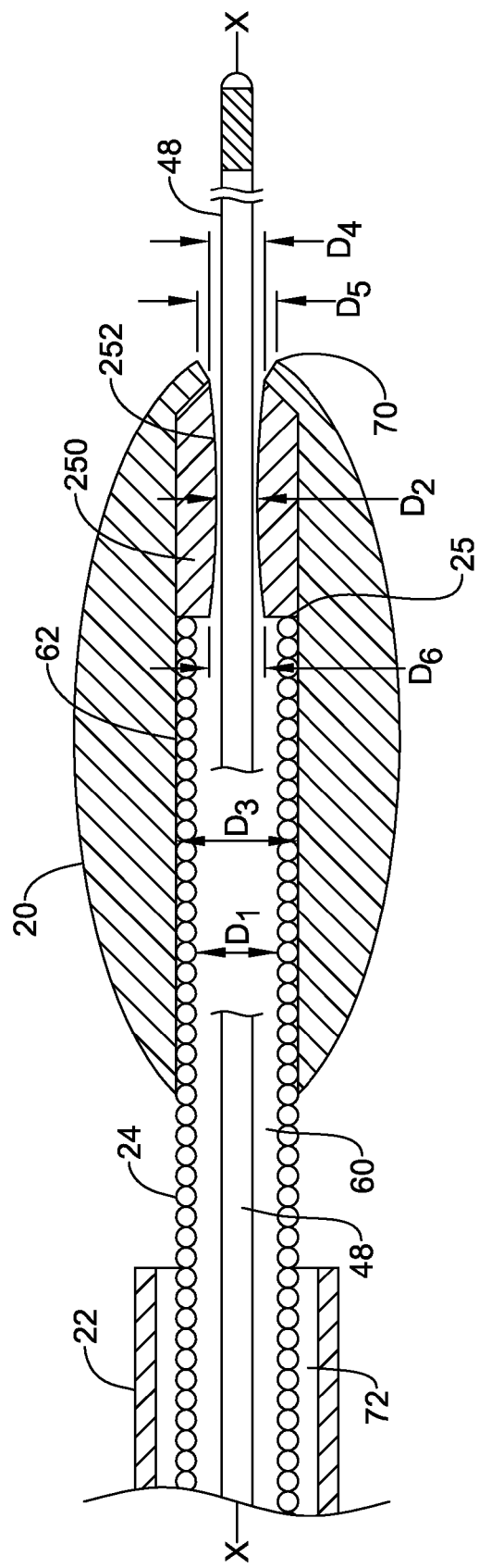
FIG. 4 is a cross-sectional view of a distal portion of another exemplary atherectomy system in accordance with the disclosure.

Another embodiment of the distal region of the rotational atherectomy device 12 is shown in FIG. 4. The components and arrangement of the distal region may be similar in many respects to that shown in FIG. 2, and thus reference to those aspects discussed above is noted. As shown in FIG. 4, an insert 250 may be positioned within the cutting member 20. For example, the insert 250 may be positioned in the bore 62 of the cutting member 20 distal of a distal end 25 of the drive shaft 24. The insert 250 may include an opening 252 extending therethrough for passing the guidewire 48 therethrough. In some instances, the opening 252 through the insert 250 may be axially aligned with the guidewire lumen 60 of the drive shaft 24. In other words, the opening 252 may be coaxial with the guidewire lumen 60 in some instances.

The insert 250 may include an inner surface defining the opening 252 of the insert 250. As shown in FIG. 4, at least a portion of the inner surface of the insert 250 may be nonparallel to the central longitudinal axis X of the drive shaft 24. For example, the inner surface of the insert 250 may taper radially outward from the central longitudinal axis in a distal direction (i.e., flare radially outward toward the distal tip 70) along at least a portion of the longitudinal length of the opening 252. For example, a mid region of the opening 252 may have a diameter $D_2$, while a distal region of the opening 252 may have a diameter $D_4$ greater than the diameter $D_2$ of the mid region of the opening 252. Furthermore, the inner surface of the insert 250 may taper radially outward from the central longitudinal axis in a proximal direction (i.e., flare radially outward toward the proximal end of the insert 250) along at least a portion of the longitudinal length of the opening 252. For example, a proximal region of the opening 252 may have a diameter $D_6$ greater than the diameter $D_2$ of the mid region of the opening 252. In some instances the diameter $D_6$ of the proximal region of the opening 252 may be the same as the diameter $D_4$ of the distal region of the opening 252, or the diameter $D_6$ may be different than (e.g., greater than or less than) the diameter $D_4$.

The insert 250 may be similar to the insert 50 described above. For example, the insert 250 may function as a spacer and/or bearing between the cutting member 20 and the guidewire 48. For example, the insert 250 may provide a low friction interface with the guidewire 48 as the cutting member 20 is rotatably driven during a medical procedure.

In some instances, the inner surface of the insert 250 which defines the opening 252 of the insert 250 may have an average surface roughness $R_a$ of about 0.4 micrometers or less, about 0.3 micrometers or less, about 0.2 micrometers or less, or about 0.1 micrometers or less. Additionally or alternatively, in some instances the coefficient of static friction $\mu_s$ between the insert 250 and the guidewire 48 may be less than 0.25, less than 0.20, less than 0.15 or less than 0.10, for example.

The insert 250 may be made of any desired material, such as a low friction material, including a metallic material, a polymeric material, or a combination thereof. Some suitable metallic materials include stainless steel, such as highly polished stainless steel. Some suitable polymeric materials include polyamide (e.g., nylon), polytetrafluoroethylene (PTFE), high density polyethylene (HDPE), ultra-high molecular weight polyethylene (UHMWPE), or other polymeric material having a high molecular weight, for example.

Also shown in FIG. 4, the distal opening of the cutting member 20 at the distal tip 70 may have a diameter $D_5$ greater than the diameter $D_4$ of the distal region of the opening 252, and thus greater than the diameter $D_2$ of the mid region of the opening 252. The enlarged diameter of the distal opening of the cutting member 20 may facilitate inserting the guidewire 48 into the opening 252 of the insert 250 and through the guidewire lumen 62 of the drive shaft 24 from the distal tip 70 of the cutting member 20.

Figure 5:
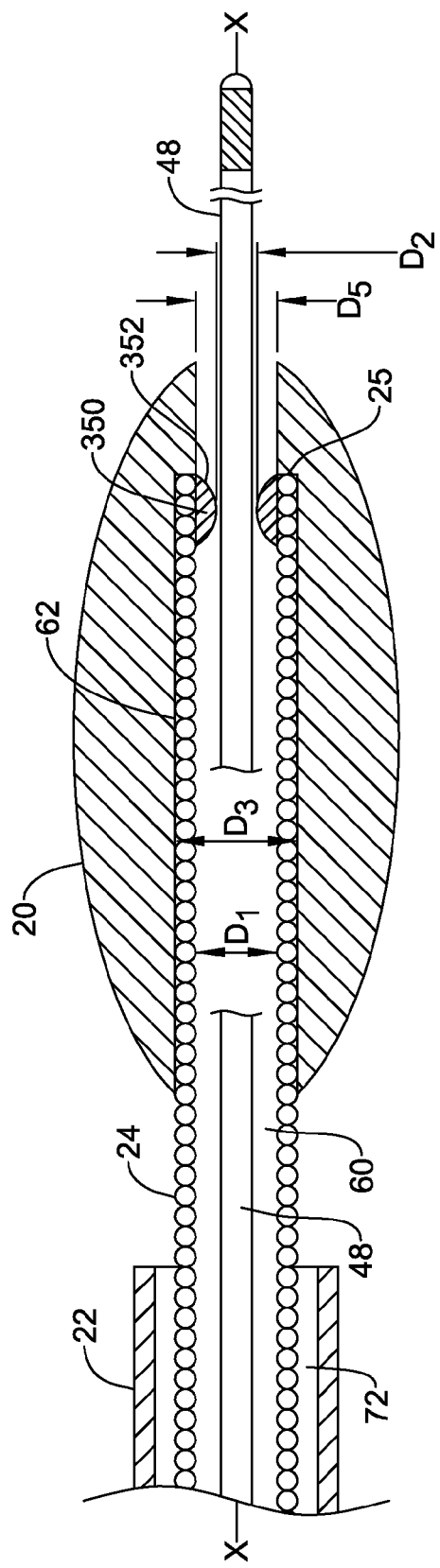
FIG. 5 is a cross-sectional view of a distal portion of another exemplary atherectomy system in accordance with the disclosure.

Another embodiment of the distal region of the rotational atherectomy device 12 is shown in FIG. 5. The components and arrangement of the distal region may be similar in many respects to that shown in FIG. 2, and thus reference to those aspects discussed above is noted. As shown in FIG. 5, an insert 350 may be positioned within the cutting member 20. For example, the insert 350 may be positioned in the bore 62 of the cutting member 20 within the distal end region of the drive shaft 24. The insert 350 may include an opening 352 extending therethrough for passing the guidewire 48 therethrough. In some instances, the opening 352 through the insert 350 may be axially aligned with the guidewire lumen 60 of the drive shaft 24. In other words, the opening 352 may be coaxial with the guidewire lumen 60 in some instances.

The insert 350 may include an inner surface defining the opening 352 of the insert 350. As shown in FIG. 5, at least a portion of the inner surface of the insert 350 may be nonparallel to the central longitudinal axis X of the drive shaft 24. For example, the inner surface of the insert 350 may taper radially outward from the central longitudinal axis in a distal direction (i.e., flare radially outward toward its distal end) along at least a portion of the longitudinal length of the opening 352 and/or may taper radially outward from the central longitudinal axis in a proximal direction (i.e., flare radially outward toward its proximal end). For example, a mid region of the opening 352 may have a diameter $D_2$, while a proximal region and/or a distal region of the opening 352 may have a diameter greater than the diameter $D_2$ of the mid region of the opening 352.

The insert 350 may be similar to the insert 50 described above. For example, the insert 350 may function as a spacer and/or bearing between the cutting member 20 and the guidewire 48. For example, the insert 350 may provide a low friction interface with the guidewire 48 as the cutting member 20 is rotatably driven during a medical procedure.

In some instances, the inner surface of the insert 350 which defines the opening 352 of the insert 350 may have an average surface roughness $R_a$ of about 0.4 micrometers or less, about 0.3 micrometers or less, about 0.2 micrometers or less, or about 0.1 micrometers or less. Additionally or alternatively, in some instances the coefficient of static friction $\mu_s$ between the insert 350 and the guidewire 48 may be less than 0.25, less than 0.20, less than 0.15 or less than 0.10, for example.

The insert 350 may be made of any desired material, such as a low friction material, including a metallic material, a polymeric material, or a combination thereof. Some suitable metallic materials include stainless steel, such as highly polished stainless steel. Some suitable polymeric materials include polyamide (e.g., nylon), polytetrafluoroethylene (PTFE), high density polyethylene (HDPE), ultra-high molecular weight polyethylene (UHMWPE), or other polymeric material having a high molecular weight, for example.

Also shown in FIG. 5, the distal opening of the cutting member 20 at the distal tip 70 may have a diameter $D_5$ greater than the diameter $D_2$ of the opening 352. The enlarged diameter of the distal opening of the cutting member 20 may facilitate inserting the guidewire 48 into the opening 352 of the insert 350 and through the guidewire lumen 62 of the drive shaft 24 from the distal tip 70 of the cutting member 20.

As shown in FIG. 5, the bore 62 of the cutting member 20 may include a stepped region between the diameter $D_3$ and the diameter $D_4$. In some instances, the distal end 25 of the drive shaft 24 and/or the distal end of the insert 350 may be positioned adjacent to and/or abut the stepped region of the bore 62.

Although the central longitudinal axis of the cutting member 20 and the central longitudinal axis of the insert 50, 150, 250, 350 are shown in FIGS. 2-5 as being coaxial with the central longitudinal axis X (i.e., the rotational axis) of the drive shaft 24, in other instances, the central longitudinal axis of the cutting member 20 and/or the central longitudinal axis of the insert 50, 150, 250, 350 may be non-coaxial with the central longitudinal axis X of the drive shaft 24, allowing for eccentric rotation of the cutting member 20 while still providing a smooth bearing surface inside the cutting member 20 for the guidewire 48.

Figure 6:
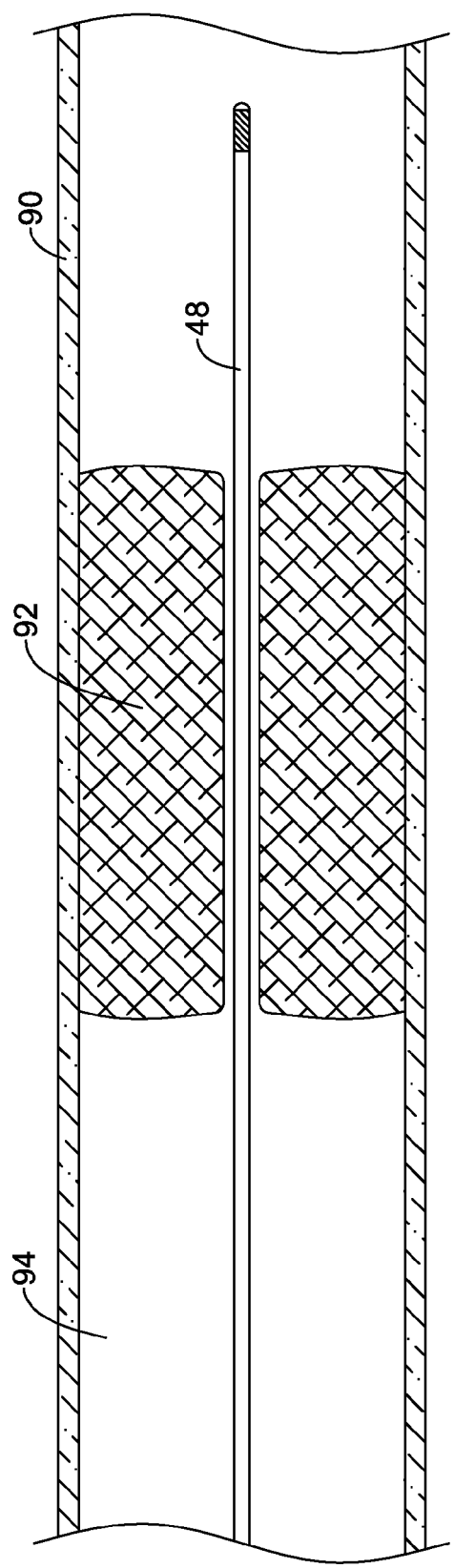
FIGS. 6-12 illustrate aspects of an exemplary method of traversing an occlusion in a blood vessel.

Turning now to FIGS. 6-12, aspects of an exemplary method of traversing an occlusion in a blood vessel are shown. As shown in FIG. 6, a guidewire 48 may be advanced through the lumen 94 of the blood vessel 90 to a location proximate an occlusion 92. For instance, the guidewire 48 may be advanced through the occlusion 92 such that the distal end of the guidewire 48 passes distally beyond the occlusion 92.

Figure 7:
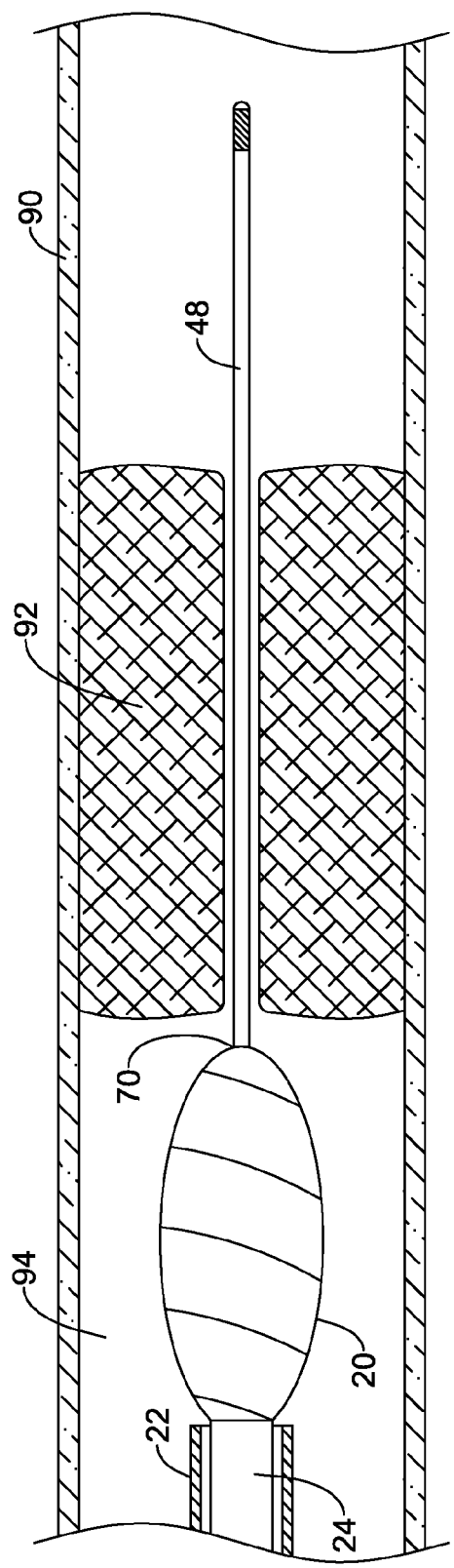
Figure 8:
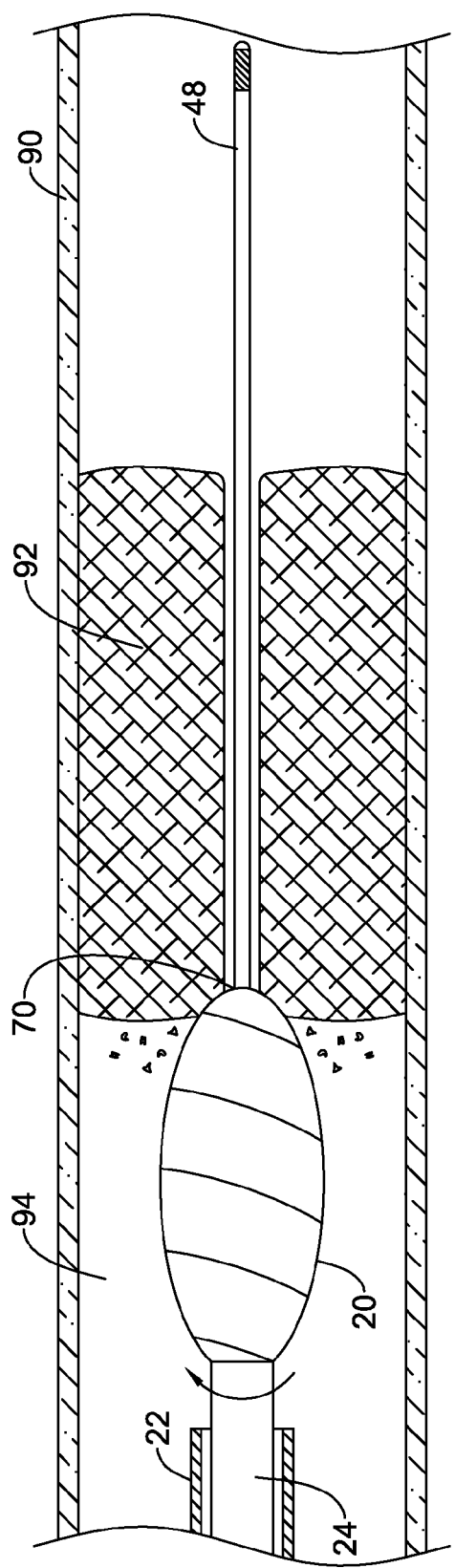

Referring to FIG. 7, the rotational atherectomy device 12 may then be advanced through the lumen 94 of the blood vessel 90 over the guidewire 48 to a location proximate the occlusion 92 to create or enlarge a passageway through the occlusion 92. For instance, the elongate shaft 18 of the rotational atherectomy device 12 may be advanced through a body lumen (e.g., blood vessel 90) to a location proximal of the occlusion 92 in the body lumen. For example, the guidewire 48 may pass into the distal opening of the cutting member 20, through the opening 52, 152, 252, 352 of the insert 50, 150, 250, 350 within the cutting member 20, and through the guidewire lumen 60 of the drive shaft 24, as shown in FIGS. 2-5. In some instances, the elongate shaft 18 may be advanced through a lumen of a guide catheter to the occlusion 92 while being advanced along the guidewire 48.

Once positioned proximate the occlusion 92, the rotational atherectomy device 12 may be used to create or enlarge a passageway through the occlusion 92. For example, referring to FIG. 8, thereafter, rotation of the cutting member 20 (via rotationally driving the drive shaft 24) may be initiated once the cutting member 20 has been advanced to the occlusion 92. The rotatable drive shaft 24 extending through the outer tubular member 22 of the elongate shaft 18 of the rotational atherectomy device 12 may be rotatably driven to rotatably drive the cutting member 20 while advancing the cutting member 20 through the occlusion 92. In some instances the drive shaft 24 may be advanced distally relative to the outer tubular member 22 to advance the cutting member 20 through the occlusion 92, while in other instances the outer tubular member 22 may be advanced together with the drive shaft 24. In some instances, fluid infusion and/or fluid aspiration through one or more lumens of the rotational atherectomy device 12 may be performed while advancing the cutting member 20 through the occlusion 92.

The insert 50, 150, 250, 350 may function as a bearing as the cutting member 20 rotates at a high rotational rate, e.g., 5,000 revolutions per minute (RPM) or more, 10,000 revolutions per minute (RPM) or more, or 20,000 revolutions per minute (RPM) or more) about the guidewire 48. The insert 50, 150, 250, 350 may maintain the guidewire 48 spaced away from directly contacting the cutting member 20 as the cutting member 20 is being rotated about its rotational axis. The frictional interaction between the guidewire 48 and the insert 50 may be less than that between the guidewire 48 and the cutting member 20 if permitted to frictionally contact one another. In some instances the coefficient of static friction $\mu_s$ between the insert 50, 150, 250, 350 and the guidewire 48 may be less than 0.25, less than 0.20, less than 0.15 or less than 0.10, for example.

Figure 9:
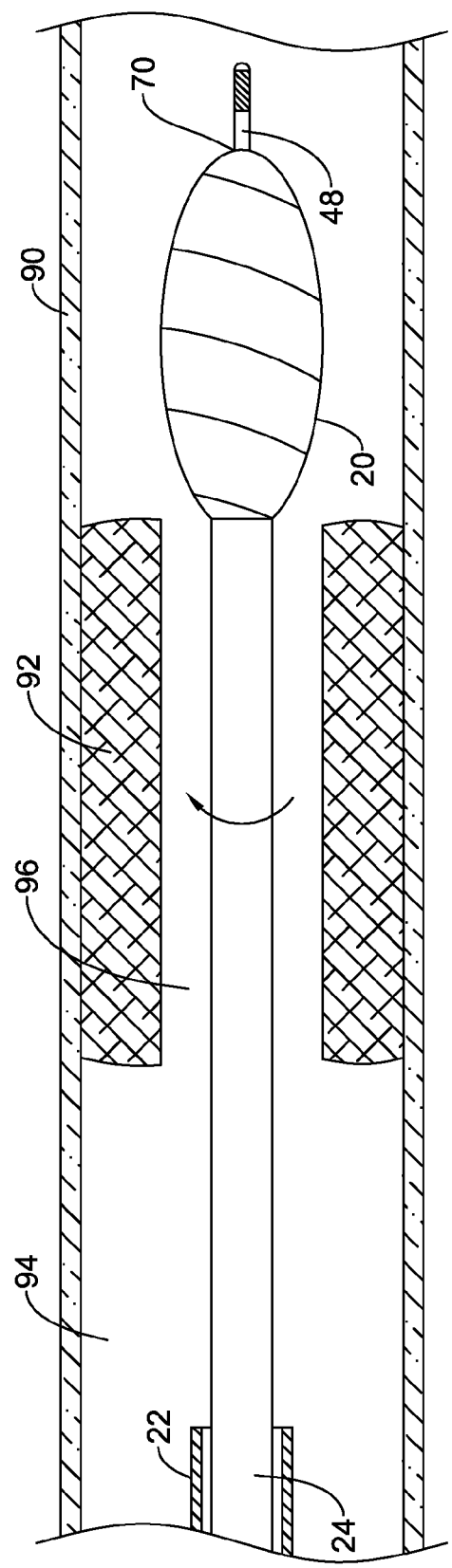
Figure 10:
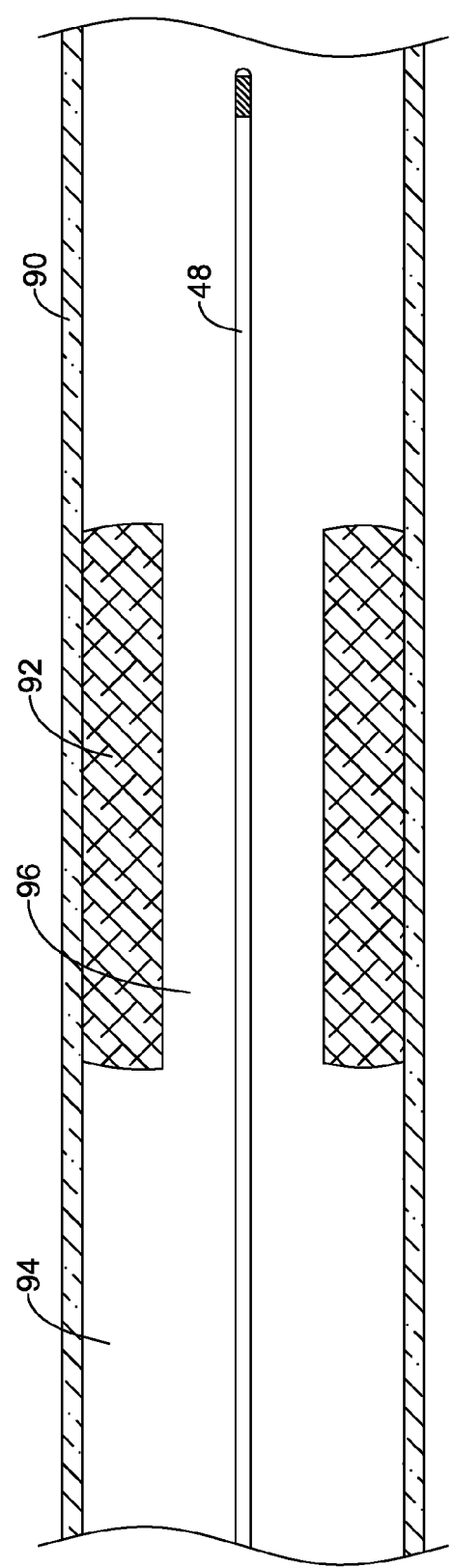
Figure 11:
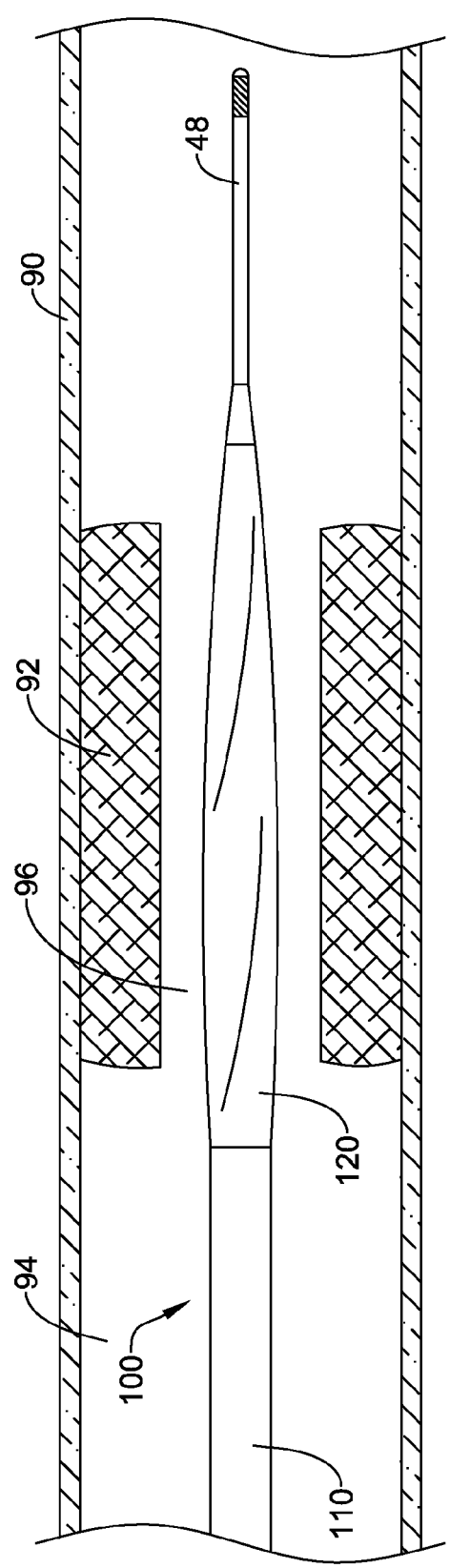
Figure 12:
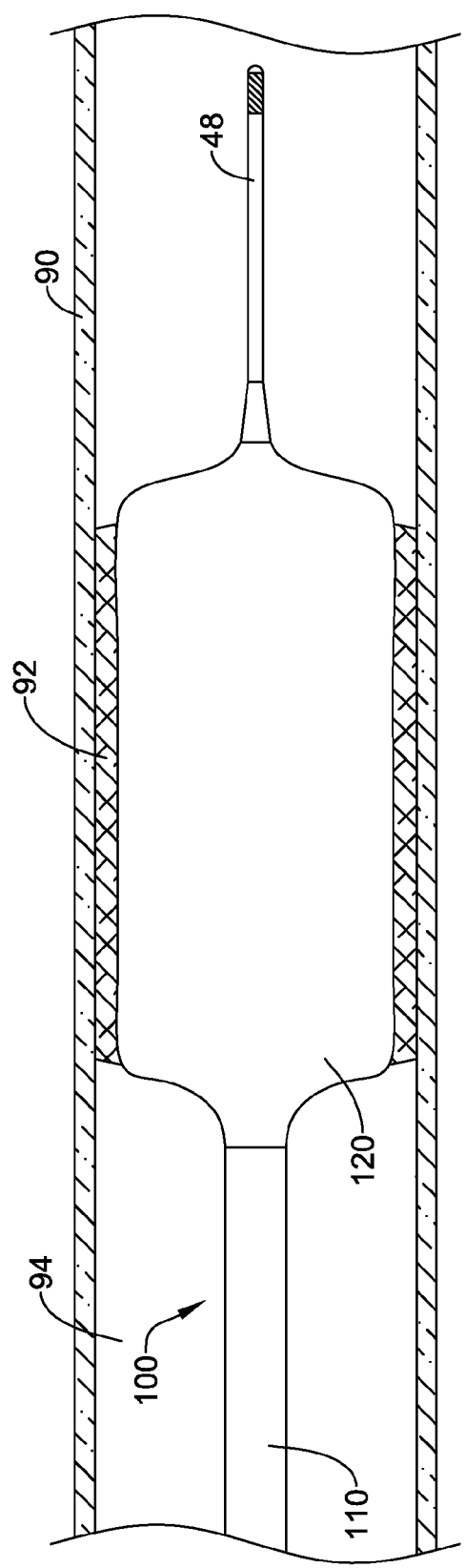

The cutting member 20 may be advanced through the occlusion 92 to form or enlarge a pathway 96 through the occlusion 92 to permit blood flow through the lumen 94 of the blood vessel 90, as shown in FIG. 9. Thereafter, as shown in FIG. 10, the rotational atherectomy device 12 may be withdrawn, leaving the guidewire 48 in position across the occlusion 92. Another intravascular device, such as a therapeutic or diagnostic medical device, may then be advanced over the guidewire 48 to a location proximate to or distal of the occlusion 92, for example. For instance, as shown in FIG. 11, an angioplasty catheter 100 may be advanced over the previously positioned guidewire 48 to position an inflatable balloon 120 of the angioplasty catheter 100 across the occlusion 92. The balloon 120 may then be inflated with an inflation media introduced into the balloon 120 from an inflation lumen extending through the elongate shaft 110 of the angioplasty catheter 100 to further enlarge the passageway through the occlusion 92.

As described above, the same guidewire 48 may be used throughout the procedure without the need to exchange the guidewire 48 for one or more other guidewires. For example, the same guidewire 48 used to initially cross the occlusion 92 may also be used in advancing the rotational atherectomy device 12 distally through the occlusion 92 and/or in advancing one or more additional intravascular devices proximate to or distally through the occlusion 92. The ability to utilize the same guidewire 48 without performing a guidewire exchange may save time during the procedure as well as reduce the number of medical devices needed to complete the procedure.

It is noted that the rotational cutting devices described herein may be used in other medical procedures, such as in orthopedic medical procedures, if desired. For example, the penetrating member may be penetrated into a bony structure to stabilize the cutting member prior to initiating engagement of the rotating cutting member with the bony structure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A rotational atherectomy device, comprising:
an outer tubular member having a lumen extending therethrough;
a cutting member rotationally positioned at a distal end of the outer tubular member;
a drive shaft extending through the lumen of the outer tubular member, the drive shaft rotatable relative to the outer tubular member to rotate the cutting member; and
an insert positioned within the cutting member, the insert including an opening extending therethrough for passing a guidewire therethrough,
wherein the insert includes an inner surface defining the opening of the insert,
wherein at least a portion of the inner surface is nonparallel to a central longitudinal axis of the drive shaft,
wherein the inner surface tapers radially outward from the central longitudinal axis in a distal direction,
wherein the cutting member is fixed to the drive shaft.

2. The rotational atherectomy device of claim 1, wherein a distal portion of the drive shaft extends into a bore of the cutting member.

3. The rotational atherectomy device of claim 2, wherein the insert is positioned in the bore of the cutting member distal of a distal end of the drive shaft.

4. The rotational atherectomy device of claim 2, wherein the drive shaft includes a guidewire lumen extending therethrough longitudinally aligned with the opening of the insert.

5. The rotational atherectomy device of claim 4, wherein the guidewire lumen has a diameter and the opening of the insert has a diameter less than the diameter of the guidewire lumen.

6. The rotational atherectomy device of claim 1, wherein the inner surface tapers radially outward in a distal direction from a mid region of the insert to a distal tip of the insert.

7. The rotational atherectomy device of claim 6, wherein the inner surface tapers radially outward in a proximal direction from the mid region of the insert to a proximal end of the insert.

8. The rotational atherectomy device of claim 1, wherein the cutting member includes a distal opening axially aligned with the opening of the insert, the distal opening of the cutting member having a diameter greater than a diameter of the opening of the insert.

9. The rotational atherectomy device of claim 1, wherein the insert includes an inner surface defining the opening of the insert, the inner surface having a surface roughness $R_a$ of 0.4 micrometers or less.

10. The rotational atherectomy device of claim 1, wherein the insert includes an inner surface defining the opening of the insert, the inner surface having a surface roughness $R_a$ of 0.2 micrometers or less.

11. A rotational atherectomy device, comprising:
an outer tubular member having a lumen extending therethrough;
a cutting member rotationally positioned at a distal end of the outer tubular member, the cutting member including a central longitudinal bore extending therethrough;
an insert positioned within the bore of the cutting member, the insert including an opening extending therethrough axially aligned with the bore of the cutting member,
wherein the insert includes an inner surface defining the opening of the insert,
wherein at least a portion of the inner surface is nonparallel to a central longitudinal axis of a drive shaft, wherein the inner surface tapers radially outward from the central longitudinal axis in a distal direction; and a drive shaft extending through the lumen of the outer tubular member, a distal end region of the drive shaft extending into the bore of the cutting member with a distal end of the drive shaft abutting a proximal end of the insert, the drive shaft rotatable relative to the outer tubular member to rotate the cutting member;

wherein the cutting member is fixed to the drive shaft.

12. The rotational atherectomy device of claim 11, wherein the drive shaft includes a guidewire lumen extending therethrough axially aligned with the opening of the insert.

13. The rotational atherectomy device of claim 12, wherein the guidewire lumen has a diameter and the opening of the insert has a diameter less than the diameter of the guidewire lumen.

14. The rotational atherectomy device of claim 11, wherein the cutting member includes a distal opening axially aligned with the opening of the insert, the distal opening of the cutting member having a diameter greater than or equal to a diameter of the distal opening of the insert.

15. The rotational atherectomy device of claim 11, wherein the insert includes an inner surface defining the opening of the insert, the inner surface having a surface roughness $R_a$ of 0.4 micrometers or less.

16. A method of creating or enlarging a passageway through an occlusion in a body lumen, comprising:

advancing a guidewire through a body lumen to a location proximate an occlusion;

advancing a rotational atherectomy device through the body lumen over the guidewire to a location proximal of the occlusion in the body lumen, the rotational atherectomy device including a rotatable drive shaft extending through an outer tubular member to rotatably drive a cutting member positioned at a distal end of the outer tubular member, and an insert positioned within the cutting member, wherein the guidewire extends through an opening of the insert and a guidewire lumen of the drive shaft, wherein the insert includes an inner surface defining the opening of the insert, wherein at least a portion of the inner surface is nonparallel to a central longitudinal axis of the drive shaft, wherein the inner surface tapers radially outward from the central longitudinal axis in a distal direction; and rotating the cutting member relative to the guidewire with the drive shaft while advancing the cutting member through the occlusion, wherein the cutting member is fixed to the drive shaft.

17. The method of claim 16, wherein a coefficient of static friction between the insert and the guidewire is less than 0.25.

* * * * *